(12) United States Patent  
Smith et al.

(10) Patent No.: US 9,314,287 B2
(45) Date of Patent: Apr. 19, 2016

(54) ASSEMBLY TOOL FOR MODULAR IMPLANT AND ASSOCIATED METHOD

(71) Applicant: Biomet Manufacturing, LLC, Warsaw, IN (US)

(72) Inventors: Aaron P. Smith, Warsaw, IN (US); Tyler D. Witt, Warsaw, IN (US); Andrew Freiberg, Weston, MA (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 450 days.

(21) Appl. No.: 13/861,149

(22) Filed: Apr. 11, 2013

(65) Prior Publication Data

US 2013/0231674 A1  Sep. 5, 2013

Related U.S. Application Data

(62) Division of application No. 12/718,027, filed on Mar. 5, 2010, now Pat. No. 8,419,743.

(51) Int. Cl.
  *A61B 17/88* (2006.01)
  *A61B 17/56* (2006.01)

(52) U.S. Cl.
  CPC .............. *A61B 17/88* (2013.01); *A61B 17/56* (2013.01)

(58) Field of Classification Search
  CPC ....................................................... A61B 17/88
  See application file for complete search history.

(56) References Cited

U.S. PATENT DOCUMENTS

| | | |
|---|---|---|
| 1,714,684 A | 5/1929 | Malcolm |
| 2,231,864 A | 2/1941 | Abel |
| 3,815,599 A | 6/1974 | Deyerle |
| 4,012,796 A | 3/1977 | Weisman et al. |
| 4,306,550 A | 12/1981 | Forte |
| 4,535,487 A | 8/1985 | Esper et al. |
| 4,549,319 A | 10/1985 | Meyer |
| 4,552,136 A | 11/1985 | Kenna |
| 4,601,289 A | 7/1986 | Chiarizzio et al. |
| 4,718,915 A | 1/1988 | Epinette |

(Continued)

FOREIGN PATENT DOCUMENTS

| | | |
|---|---|---|
| DE | 29516473 U1 | 12/1995 |
| EP | 0453695 A1 | 10/1991 |

(Continued)

OTHER PUBLICATIONS

DePuy, a Johnson & Johnson company, "REEF: Distally Interlocked Modular Femoral Reconstruction Prosthesis", 2004, 7 sheets.

(Continued)

*Primary Examiner* — David Bates
(74) *Attorney, Agent, or Firm* — Schwegman Lundberg & Woessner, P.A.

(57) ABSTRACT

A method of implanting a modular implant having a proximal implant and a distal implant into an anatomic site includes sequentially assembling a plurality of components of an assembly tool on to the proximal and distal implants and holding corresponding tapers of the proximal and distal implants separated by a selected separation distance by the assembly tool. The method also includes impacting the proximal and distal implants to an anatomic depth without changing the separation distance by impacting the assembly tool, and actuating the assembly tool to lock the corresponding tapers of the proximal and distal implants without removing the assembly tool.

20 Claims, 14 Drawing Sheets

(56) References Cited

U.S. PATENT DOCUMENTS

| | | | |
|---|---|---|---|
| 4,728,333 | A | 3/1988 | Masse et al. |
| 4,770,660 | A | 9/1988 | Averill |
| 4,790,852 | A | 12/1988 | Noiles |
| 4,842,606 | A | 6/1989 | Kranz et al. |
| 4,883,492 | A | 11/1989 | Frey et al. |
| 4,904,269 | A | 2/1990 | Elloy et al. |
| 4,959,066 | A | 9/1990 | Dunn et al. |
| 5,041,118 | A | 8/1991 | Wasilewski |
| 5,047,035 | A | 9/1991 | Mikhail et al. |
| 5,061,271 | A | 10/1991 | Van Zile |
| 5,080,685 | A | 1/1992 | Bolesky et al. |
| 5,089,004 | A | 2/1992 | Averill et al. |
| 5,092,900 | A | 3/1992 | Marchetti et al. |
| 5,122,146 | A | 6/1992 | Chapman et al. |
| 5,201,769 | A | 4/1993 | Schutzer |
| 5,211,666 | A | 5/1993 | Fetto |
| 5,376,124 | A | 12/1994 | Gustke et al. |
| 5,409,492 | A | 4/1995 | Jones et al. |
| 5,468,243 | A | 11/1995 | Halpern |
| 5,489,284 | A | 2/1996 | James et al. |
| 5,562,666 | A | 10/1996 | Brumfield |
| 5,571,111 | A | 11/1996 | Aboczky |
| 5,578,037 | A | 11/1996 | Sanders et al. |
| 5,601,564 | A | 2/1997 | Gustilo et al. |
| 5,607,431 | A | 3/1997 | Dudasik et al. |
| 5,624,445 | A | 4/1997 | Burke |
| 5,632,747 | A | 5/1997 | Scarborough et al. |
| 5,645,549 | A | 7/1997 | Boyd et al. |
| 5,649,930 | A | 7/1997 | Kertzner |
| 5,665,090 | A | 9/1997 | Rockwood et al. |
| 5,683,470 | A | 11/1997 | Johnson et al. |
| 5,690,636 | A | 11/1997 | Wildgoose et al. |
| 5,699,915 | A | 12/1997 | Berger et al. |
| 5,704,940 | A | 1/1998 | Garosi |
| 5,766,261 | A | 6/1998 | Neal et al. |
| 5,766,262 | A | 6/1998 | Mikhail |
| 5,776,194 | A | 7/1998 | Mikol et al. |
| 5,788,701 | A | 8/1998 | McCue |
| 5,849,015 | A | 12/1998 | Haywood et al. |
| 5,860,969 | A | 1/1999 | White et al. |
| 5,860,982 | A | 1/1999 | Ro et al. |
| 5,908,423 | A | 6/1999 | Kashuba et al. |
| 5,913,860 | A | 6/1999 | Scholl |
| 5,976,145 | A | 11/1999 | Kennefick, III |
| 5,989,261 | A | 11/1999 | Walker et al. |
| 6,022,357 | A | 2/2000 | Reu et al. |
| 6,027,505 | A | 2/2000 | Peter et al. |
| 6,033,405 | A | 3/2000 | Winslow et al. |
| 6,066,173 | A | 5/2000 | McKernan et al. |
| 6,110,179 | A | 8/2000 | Flivik et al. |
| 6,110,211 | A | 8/2000 | Weiss |
| 6,113,604 | A | 9/2000 | Whittaker et al. |
| 6,117,138 | A | 9/2000 | Burrows et al. |
| 6,117,173 | A | 9/2000 | Taddia et al. |
| 6,126,694 | A | 10/2000 | Gray, Jr. |
| 6,136,035 | A | 10/2000 | Lob et al. |
| 6,139,551 | A | 10/2000 | Michelson et al. |
| 6,143,030 | A | 11/2000 | Schroder |
| 6,152,963 | A | 11/2000 | Noiles et al. |
| RE37,005 | E | 12/2000 | Michelson et al. |
| 6,159,216 | A | 12/2000 | Burkinshaw et al. |
| 6,206,884 | B1 | 3/2001 | Masini |
| 6,224,605 | B1 | 5/2001 | Anderson et al. |
| 6,224,609 | B1 | 5/2001 | Ressemann et al. |
| 6,238,435 | B1 | 5/2001 | Meulink et al. |
| 6,245,111 | B1 | 6/2001 | Shaffner |
| 6,267,785 | B1 | 7/2001 | Masini |
| 6,302,890 | B1 | 10/2001 | Leone, Jr. |
| 6,306,174 | B1 | 10/2001 | Gie et al. |
| 6,325,804 | B1 | 12/2001 | Wenstrom, Jr. et al. |
| 6,330,845 | B1 * | 12/2001 | Meulink .................. 81/462 |
| 6,338,734 | B1 | 1/2002 | Burke et al. |
| 6,344,060 | B1 | 2/2002 | Schmotzer et al. |
| 6,361,565 | B1 | 3/2002 | Bonutti |
| 6,371,991 | B1 | 4/2002 | Manasas et al. |
| 6,379,384 | B1 | 4/2002 | McKernan et al. |
| 6,395,004 | B1 | 5/2002 | Dye et al. |
| 6,468,281 | B1 | 10/2002 | Badorf et al. |
| 6,517,581 | B2 | 2/2003 | Blamey |
| 6,626,913 | B1 | 9/2003 | McKinnon et al. |
| 6,871,549 | B2 | 3/2005 | Serra et al. |
| 6,875,239 | B2 | 4/2005 | Gerbec et al. |
| 6,883,217 | B2 | 4/2005 | Barrette et al. |
| 6,913,623 | B1 | 7/2005 | Zhu |
| 6,932,819 | B2 | 8/2005 | Wahl et al. |
| 7,074,224 | B2 | 7/2006 | Daniels et al. |
| 7,179,259 | B1 | 2/2007 | Gibbs |
| 7,210,881 | B2 | 5/2007 | Greenberg |
| 7,247,171 | B2 | 7/2007 | Sotereanos |
| 7,255,716 | B2 * | 8/2007 | Pubols et al. ............... 623/22.42 |
| 7,261,741 | B2 | 8/2007 | Weissman et al. |
| 7,291,176 | B2 | 11/2007 | Serra et al. |
| 7,296,804 | B2 | 11/2007 | Lechot et al. |
| 7,297,166 | B2 | 11/2007 | Dwyer et al. |
| 7,341,589 | B2 | 3/2008 | Weaver et al. |
| 7,425,214 | B1 | 9/2008 | McCarthy et al. |
| 7,491,242 | B2 | 2/2009 | Pichon et al. |
| 7,582,092 | B2 | 9/2009 | Jones et al. |
| 7,585,301 | B2 | 9/2009 | Santarella et al. |
| 7,585,329 | B2 | 9/2009 | McCleary et al. |
| 7,832,405 | B1 | 11/2010 | Schlueter et al. |
| 7,857,858 | B2 | 12/2010 | Justin et al. |
| 7,887,539 | B2 | 2/2011 | Dunbar, Jr. et al. |
| 8,118,868 | B2 | 2/2012 | May et al. |
| 8,221,432 | B2 * | 7/2012 | Smith et al. .................... 606/99 |
| 8,226,725 | B2 | 7/2012 | Ferko |
| 8,333,807 | B2 * | 12/2012 | Smith et al. ............... 623/22.42 |
| 8,419,743 | B2 | 4/2013 | Smith |
| 8,460,393 | B2 | 6/2013 | Smith et al. |
| 8,529,569 | B2 | 9/2013 | Smith et al. |
| 8,679,130 | B2 | 3/2014 | Smith et al. |
| 2003/0233100 | A1 | 12/2003 | Santarella et al. |
| 2004/0107001 | A1 | 6/2004 | Cheal et al. |
| 2004/0122439 | A1 | 6/2004 | Dwyer et al. |
| 2004/0236341 | A1 | 11/2004 | Petersen |
| 2004/0267267 | A1 | 12/2004 | Daniels et al. |
| 2005/0149042 | A1 | 7/2005 | Metzger |
| 2005/0203539 | A1 | 9/2005 | Grimm et al. |
| 2005/0234463 | A1 | 10/2005 | Hershberger et al. |
| 2006/0004459 | A1 | 1/2006 | Hazebrouck et al. |
| 2007/0093844 | A1 | 4/2007 | Dye |
| 2007/0123908 | A1 | 5/2007 | Jones et al. |
| 2007/0129809 | A1 | 6/2007 | Meridew et al. |
| 2007/0233127 | A1 | 10/2007 | Tuke et al. |
| 2008/0125867 | A1 | 5/2008 | McCleary et al. |
| 2008/0154276 | A1 | 6/2008 | Pubols et al. |
| 2008/0161811 | A1 | 7/2008 | Daniels et al. |
| 2008/0208203 | A1 | 8/2008 | Moindreau et al. |
| 2008/0234685 | A1 | 9/2008 | Gjerde |
| 2008/0243133 | A1 | 10/2008 | Heinz |
| 2008/0243190 | A1 | 10/2008 | Dziedzic et al. |
| 2008/0269765 | A1 | 10/2008 | Banerjee et al. |
| 2008/0281428 | A1 | 11/2008 | Meyers et al. |
| 2008/0294168 | A1 | 11/2008 | Wieland |
| 2009/0099566 | A1 | 4/2009 | Maness et al. |
| 2009/0112218 | A1 | 4/2009 | McCleary et al. |
| 2009/0265014 | A1 | 10/2009 | May et al. |
| 2009/0270866 | A1 | 10/2009 | Poncet |
| 2009/0307887 | A1 * | 12/2009 | Jones et al. .................... 29/281.5 |
| 2011/0015634 | A1 | 1/2011 | Smith et al. |
| 2011/0046745 | A1 | 2/2011 | Daniels et al. |
| 2011/0218583 | A1 | 9/2011 | Smith et al. |
| 2011/0218636 | A1 | 9/2011 | Smith et al. |
| 2012/0226282 | A1 | 9/2012 | Smith et al. |
| 2013/0110185 | A1 | 5/2013 | Smith et al. |
| 2013/0231674 | A1 | 9/2013 | Smith et al. |
| 2013/0274889 | A1 | 10/2013 | Smith et al. |
| 2014/0012268 | A1 | 1/2014 | Smith et al. |
| 2014/0081272 | A1 | 3/2014 | Smith et al. |
| 2014/0200619 | A1 | 7/2014 | Smith et al. |

(56) References Cited

U.S. PATENT DOCUMENTS

FOREIGN PATENT DOCUMENTS

| | | |
|---|---|---|
| FR | 2676172 A1 | 11/1992 |
| FR | 2732891 A1 | 10/1996 |
| FR | 2792822 A1 | 11/2000 |
| GB | 2299758 A | 10/1996 |
| WO | WO-94/21199 A1 | 9/1994 |
| WO | WO-2007106752 A2 | 9/2007 |

OTHER PUBLICATIONS

Zimmer, Inc., "ZMR Hip System", 2004, 19sheets.

BO10463.0 Arcos Modular Femoral Revisions System Surgical Techniques, Biomet Orthopedics, 96 pages (2010).

* cited by examiner

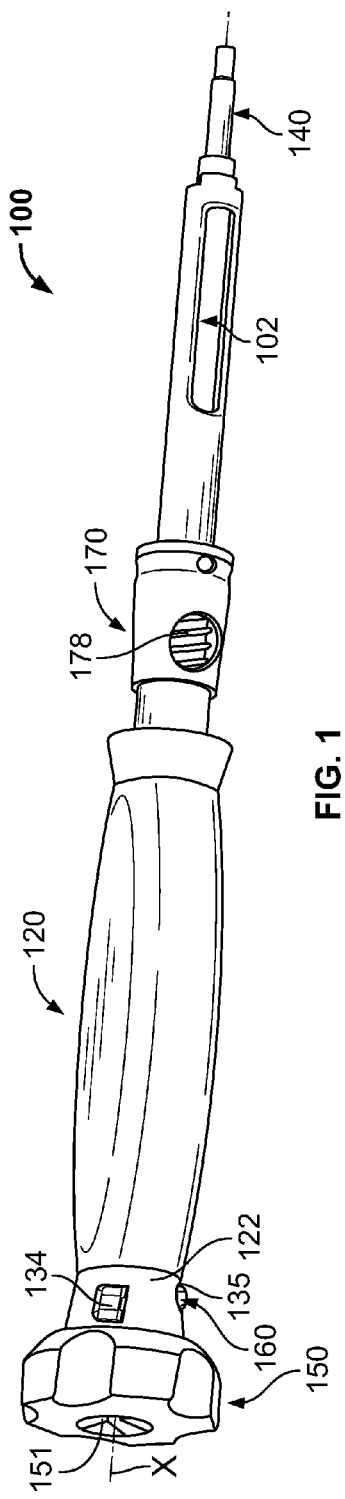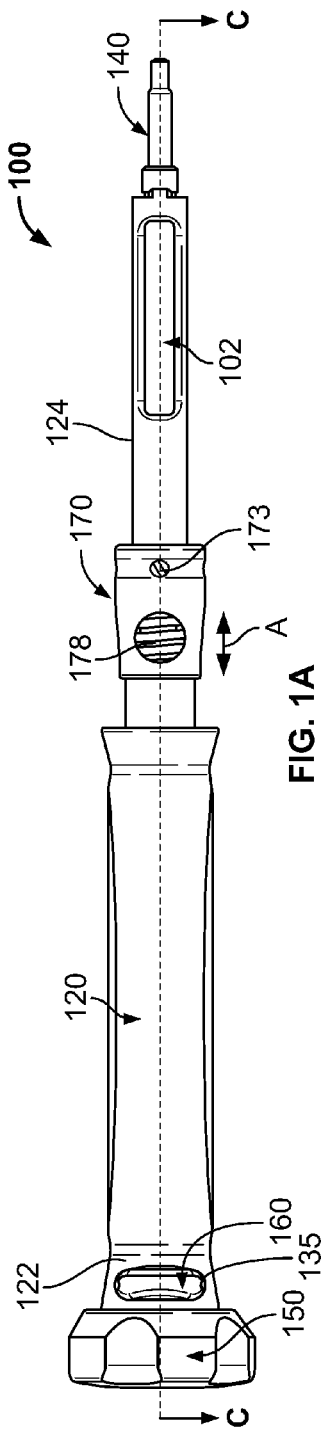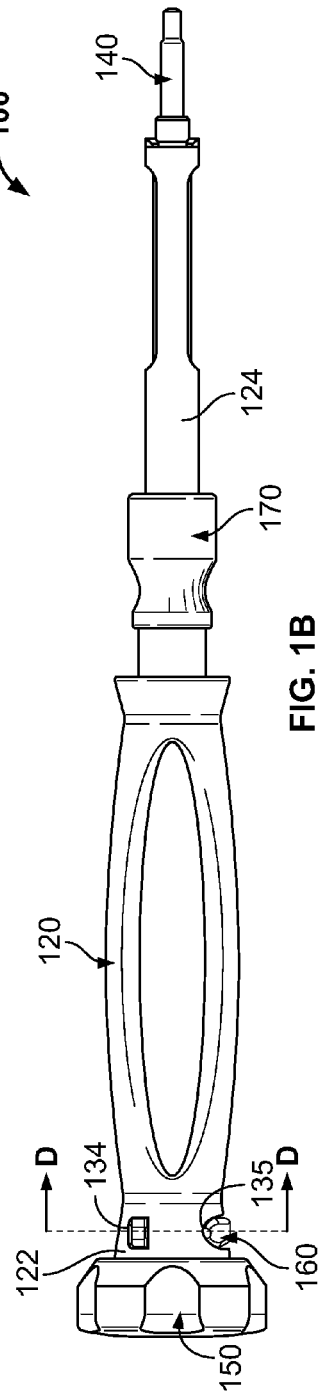

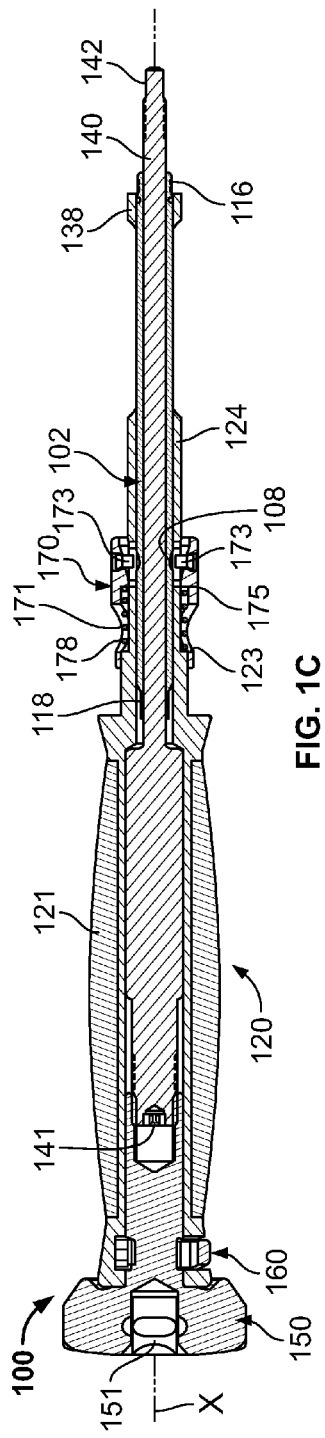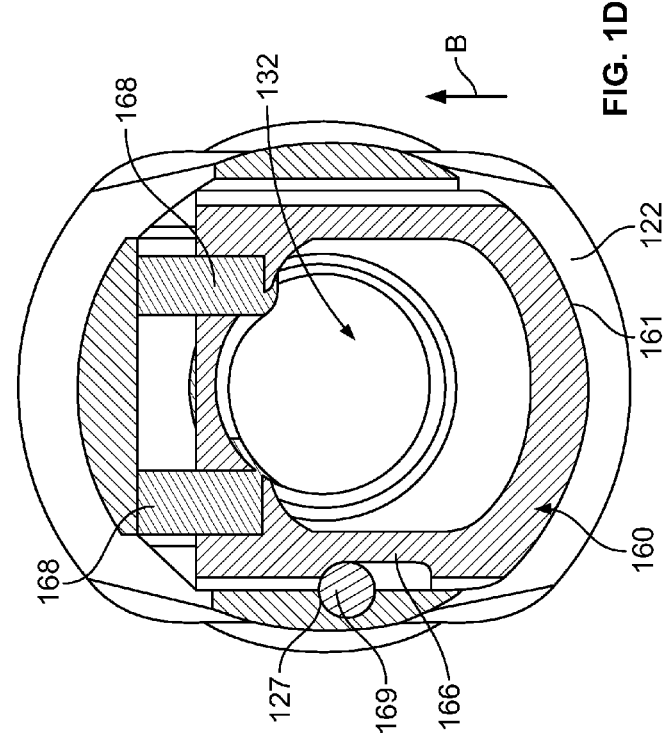
FIG. 1C
FIG. 1D

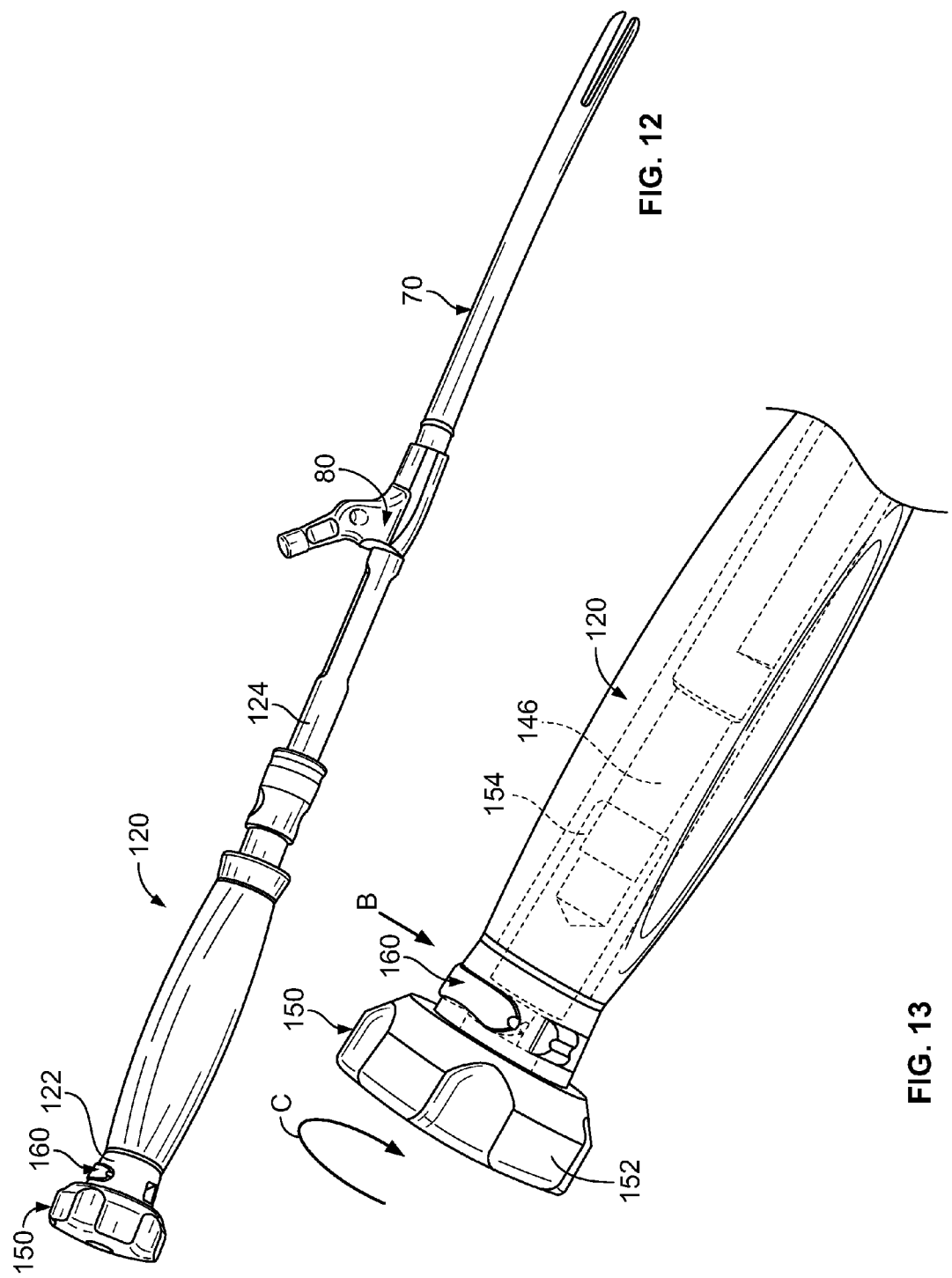

ASSEMBLY TOOL FOR MODULAR IMPLANT AND ASSOCIATED METHOD

CROSS-REFERENCE TO RELATED APPLICATIONS

This application is a divisional of U.S. patent application Ser. No. 12/718,027 filed Mar. 5, 2010.

This application is related to U.S. patent application Ser. No. 12/718,018 filed Mar. 5, 2010, now U.S. Pat. No. 8,221,432 issued Jul. 17, 2012, entitled "METHOD AND APPARATUS FOR IMPLANTING A MODULAR FEMORAL HIP;" U.S. patent application Ser. No. 12/718,230 filed Mar. 5, 2010, entitled "MODULAR LATERAL HIP AUGMENTS;" U.S. patent application Ser. No. 12/718,023 filed Mar. 5, 2010, entitled "GUIDE ASSEMBLY FOR LATERAL IMPLANTS AND ASSOCIATED METHODS;" U.S. patent application Ser. No. 12/718,026 filed Mar. 5, 2010, entitled "REVISION BROACH WITH SMOOTH LATERAL SIDE;" and U.S. patent application Ser. No. 12/718,031 filed Mar. 5, 2010, entitled "METHOD AND APPARATUS FOR TRIALING AND IMPLANTING A MODULAR FEMORAL HIP;" each filed concurrently herewith. The disclosures of each of the above applications are incorporated herein by reference.

INTRODUCTION

In femoral revision arthroplasty modular implants having separate proximal and distal components are often used. The proximal and distal components can be inserted using known assembly tools, which are then removed before locking the components together.

The present teachings provide an assembly tool for inserting and locking proximal and distal components of a modular implant.

SUMMARY

The present teachings provide an assembly tool having a proximal implant fastener, a distal implant fastener, and a compression member. The assembly tool is operable to hold in the assembled configuration a proximal implant partially engageable with a distal implant during implantation and axial impaction. Axial compaction can be exerted through the compression member of the assembly tool. The assembly tool is also operable to securely lock the tapers of the proximal and distal implants after impaction by rotating the compression member.

The present teachings also provide an assembly tool comprising a first coupler a handle member, a second coupler and a compression member. The first coupler has a first longitudinal shaft defining a first longitudinal bore and can be engaged to a proximal implant of a modular implant assembly. The handle member is removably couplable with the first coupler and the first coupler is received in a longitudinal bore of the handle member. The second coupler has a second longitudinal shaft passable through the first longitudinal bore of the first coupler. The second longitudinal shaft can be engageable to a distal implant of the modular implant through the proximal implant. The proximal implant and the distal implant are connectable with corresponding tapers. The compression member can be coupled to a proximal portion of the second longitudinal shaft and has an impaction surface. The compression member is operable to insert the proximal and distal implants to the anatomic site by impaction while holding the tapers at a selected separation distance. The compression member includes a knob. The knob is rotatable to reduce the separation distance and lock corresponding tapers of the proximal and distal implants after impaction.

The present teachings provide a method of implanting a modular implant having a proximal implant and a distal implant into an anatomic site. In one aspect, the method includes sequentially assembling a plurality of components of an assembly tool on to the proximal and distal implants and holding corresponding tapers of the proximal and distal implants separated by a selected distance by the assembly tool. The method also includes impacting the proximal and distal implants to an anatomic depth without changing the separation distance by impacting the assembly tool, and actuating the assembly tool to lock the corresponding tapers of the proximal and distal implants without removing the assembly tool.

In another aspect, the method includes engaging a distal portion of first coupler to an inner bore of the proximal implant, releasably connecting a handle member over the first coupler, passing a second coupler through the handle member and the first coupler and connecting the proximal and distal implants. The method also includes engaging a distal portion of the second coupler through the proximal implant to the distal implant, engaging a compression member to a proximal portion of the second coupler through the handle member, and rotating the compression member to hold corresponding tapers of the proximal and distal implants separated by a selected separation distance. The method also includes impacting the proximal and distal implants to an anatomic depth by impacting the compression member while holding the tapers separated by the separation distance, and rotating the compression member to lock the corresponding tapers of the proximal and distal implants without removing the compression member.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1 is an isometric view of an assembly tool according to the present teachings;

FIG. 1A is a side view of the assembly tool of FIG. 1;

FIG. 1B is a plan view of the assembly tool of FIG. 1;

FIG. 1C is a sectional view of the assembly tool of FIG. 1A taken along C-C;

FIG. 1D is a sectional view of the assembly tool of FIG. 1B taken along D-D;

FIG. 12 is an isometric view illustrating the fully assembled assembly tool holding the proximal and distal implants together according to the present teachings;

FIG. 13 is a detail of FIG. 12, illustrating rotating a compression member of the assembly tool until an audible sound is heard according to the present teachings;

DESCRIPTION OF VARIOUS ASPECTS

Figures 2, 3, 4:
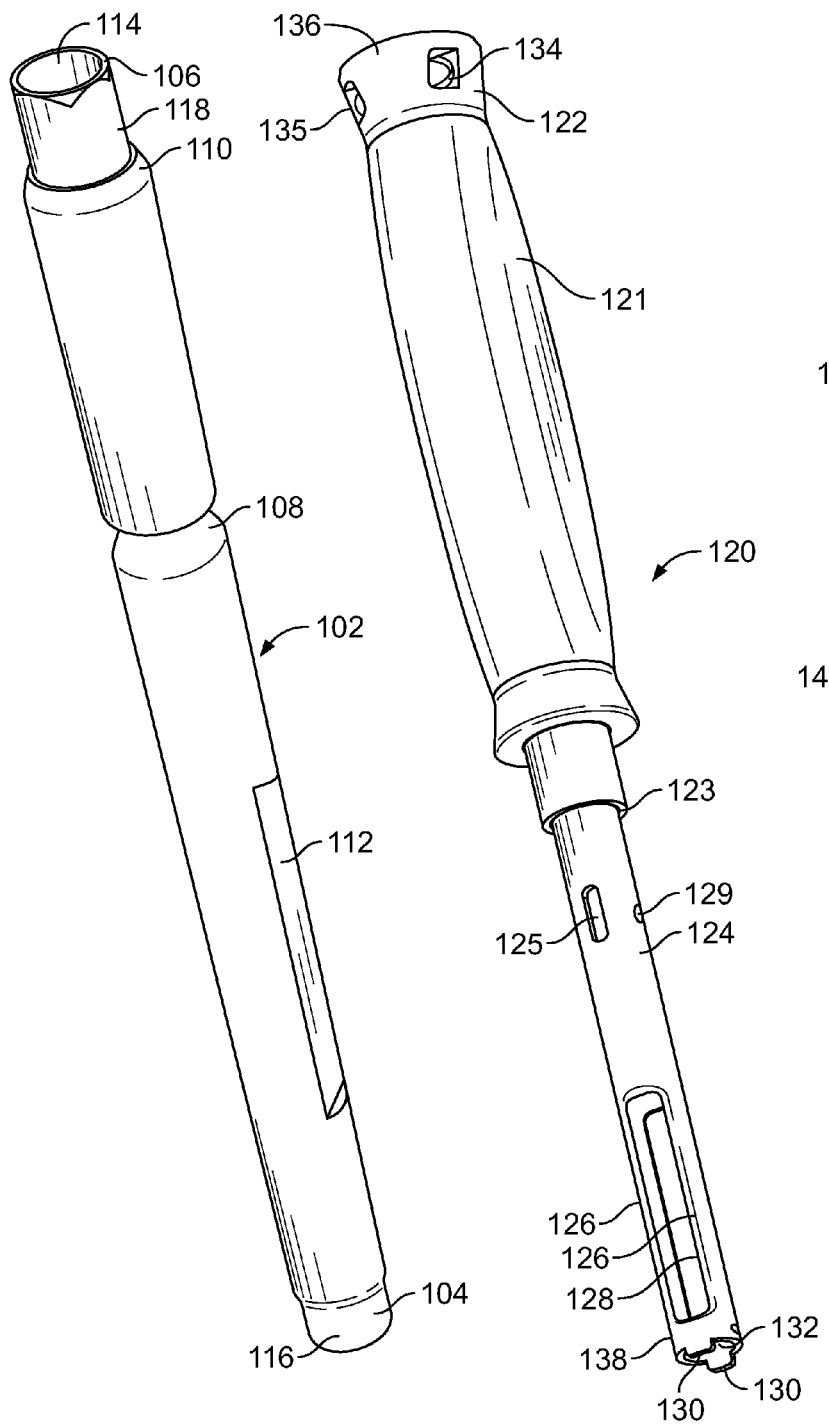
FIG. 2 is an isometric view of a proximal implant fastener of the assembly tool of FIG. 1.
FIG. 3 is an isometric view of a handle member of the assembly tool of FIG. 1.
FIG. 4 is an isometric view of a distal implant fastener of the assembly tool of FIG. 1.
Figure 5:
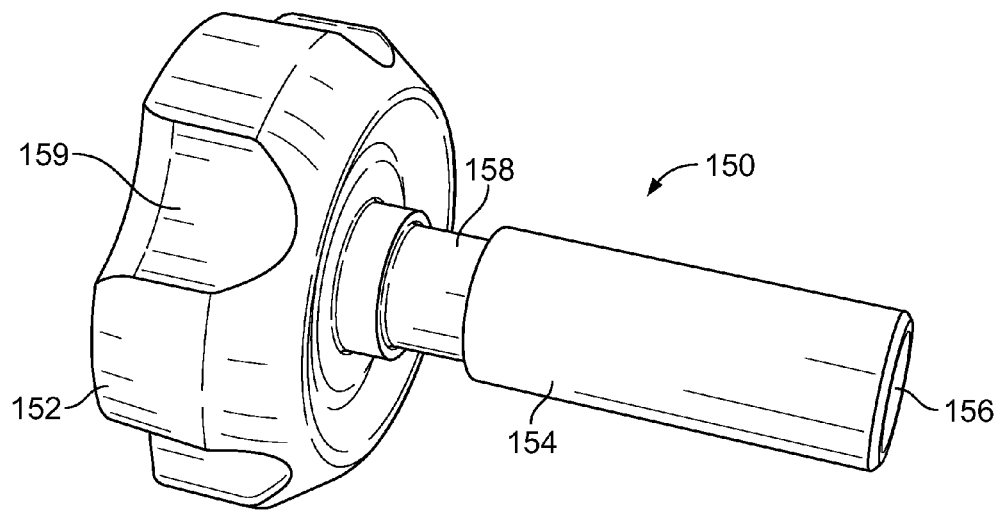
FIG. 5 is an isometric view of a compression member of the assembly tool of FIG. 1.
Figure 6:
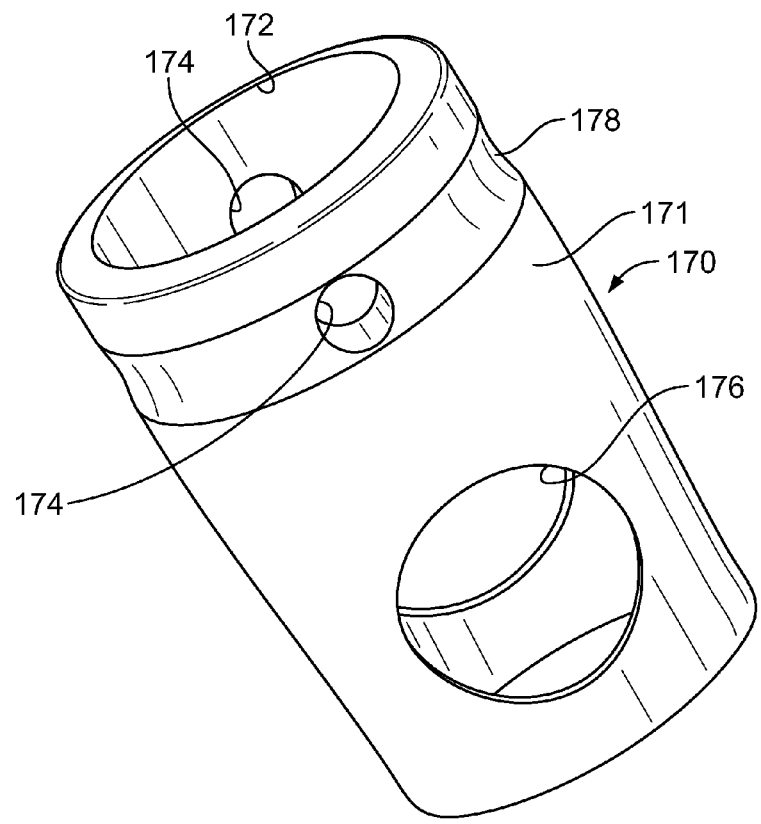
FIG. 6 is an isometric view of a sleeve of the assembly tool of FIG. 1.
Figure 7:
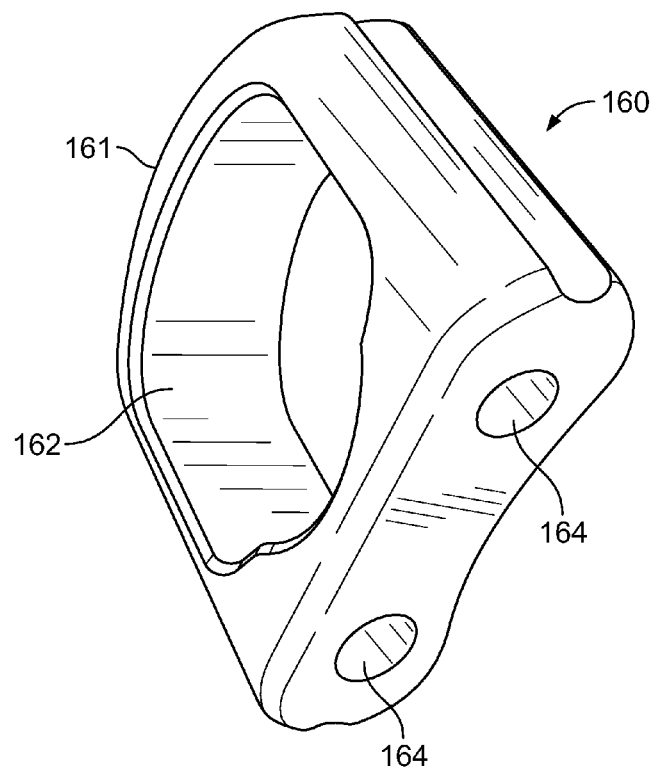
FIG. 7 is first isometric view of a slider fastener of the assembly tool of FIG. 1.

The following description is merely exemplary in nature and is in no way intended to limit the present teachings, applications, or uses. For example, although the present teachings are illustrated for hip joints in femoral revision systems, the present teachings can be used for assembling and locking modular implants for modular systems implantable in other joints, such as the knee or shoulder.

Referring to FIGS. 1, 1A-1D and 2-7, an exemplary assembly tool 100 according to the present teachings is illustrated. The assembly tool 100 can include a plurality of modularly connected components, which can be assembled onto a modular implant sequentially and, after implantation, disassembled in reverse order. The assembly tool 100 can include a handle member 120, a first coupler or proximal implant fastener 102, a second coupler or distal implant fastener 140, a slider 160, a locking member 170 and a compression cap or a compression member 150.

The handle member 120 can extend from a proximal end 136 to a distal end 138 along a longitudinal axis X and can include a handle portion 121 and a tubular shaft 124. The handle portion 121 can be molded over the tubular shaft 124, as shown in FIG. 3. Alternatively, the handle portion 121 can be removably attached to the tubular shaft 124. A through bore 132 extends through the handle member 120 from the proximal end 136 to the distal end 138 of the handle member 120. The tubular shaft 124 can include an elongated through slot 128 defined by a pair of arms 126 connected at the distal end 138. First and second anti-rotation tabs 130 can extend from the distal end 138. The anti-rotation tabs 130 allow version control during implantation, as discussed below. A proximal portion 122 of the handle member 120 can be configured for removably coupling with the compression member 150 and with the slider 160, as discussed below. The proximal portion 122 can define openings 134 facilitating cleaning and sterilizing of the handle member 120.

Figure 8:
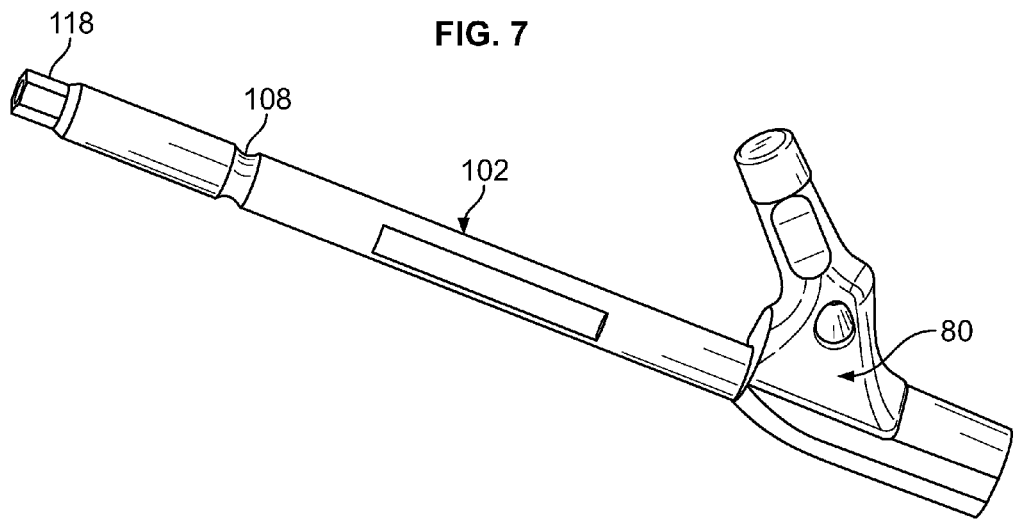
FIG. 8 is an isometric view illustrating the proximal implant fastener of FIG. 2 engaging the proximal implant according to the present teachings.
Figure 7A:
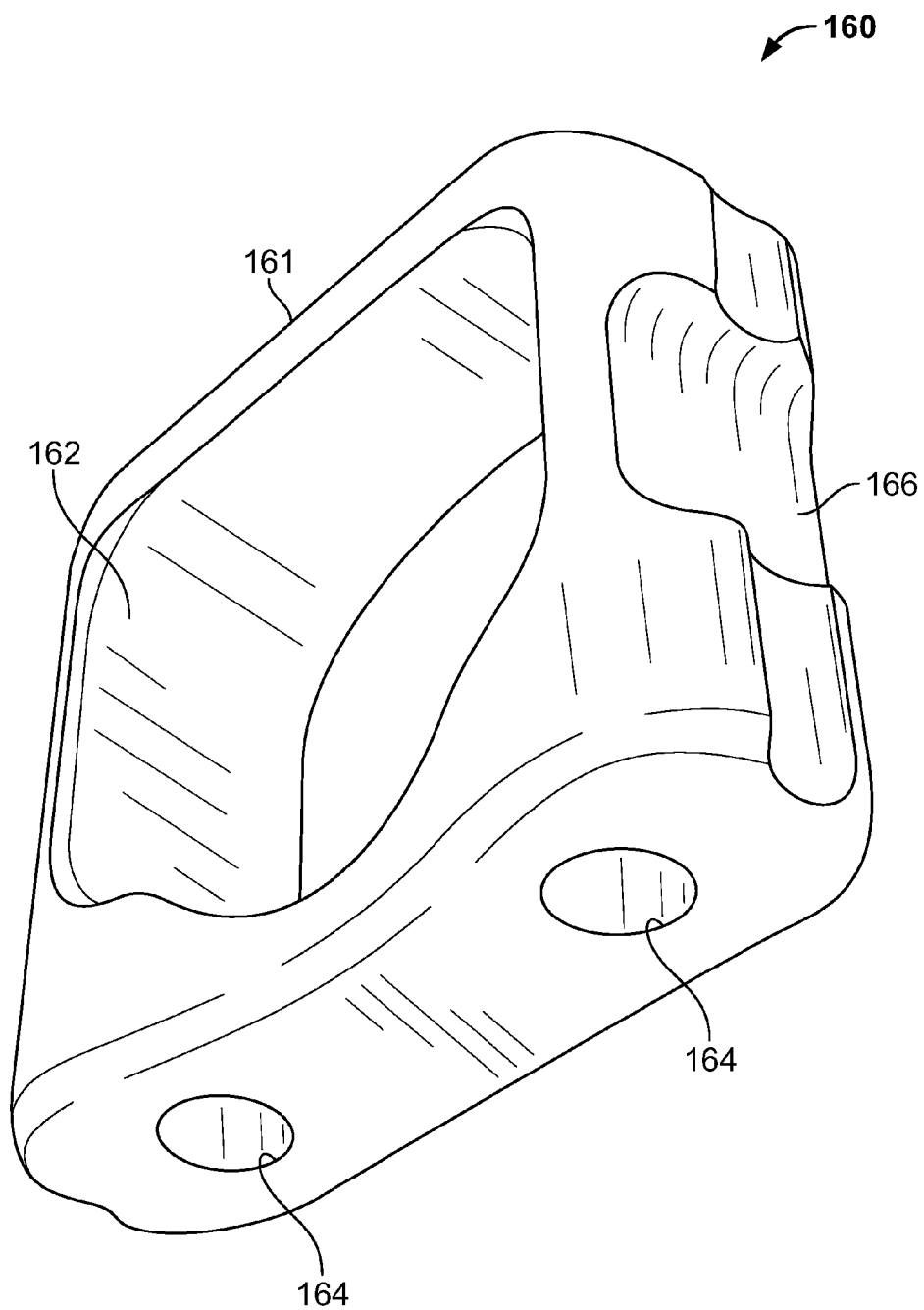
FIG. 7A is a second isometric view of a slider fastener of the assembly tool of FIG. 1.
Figure 9:
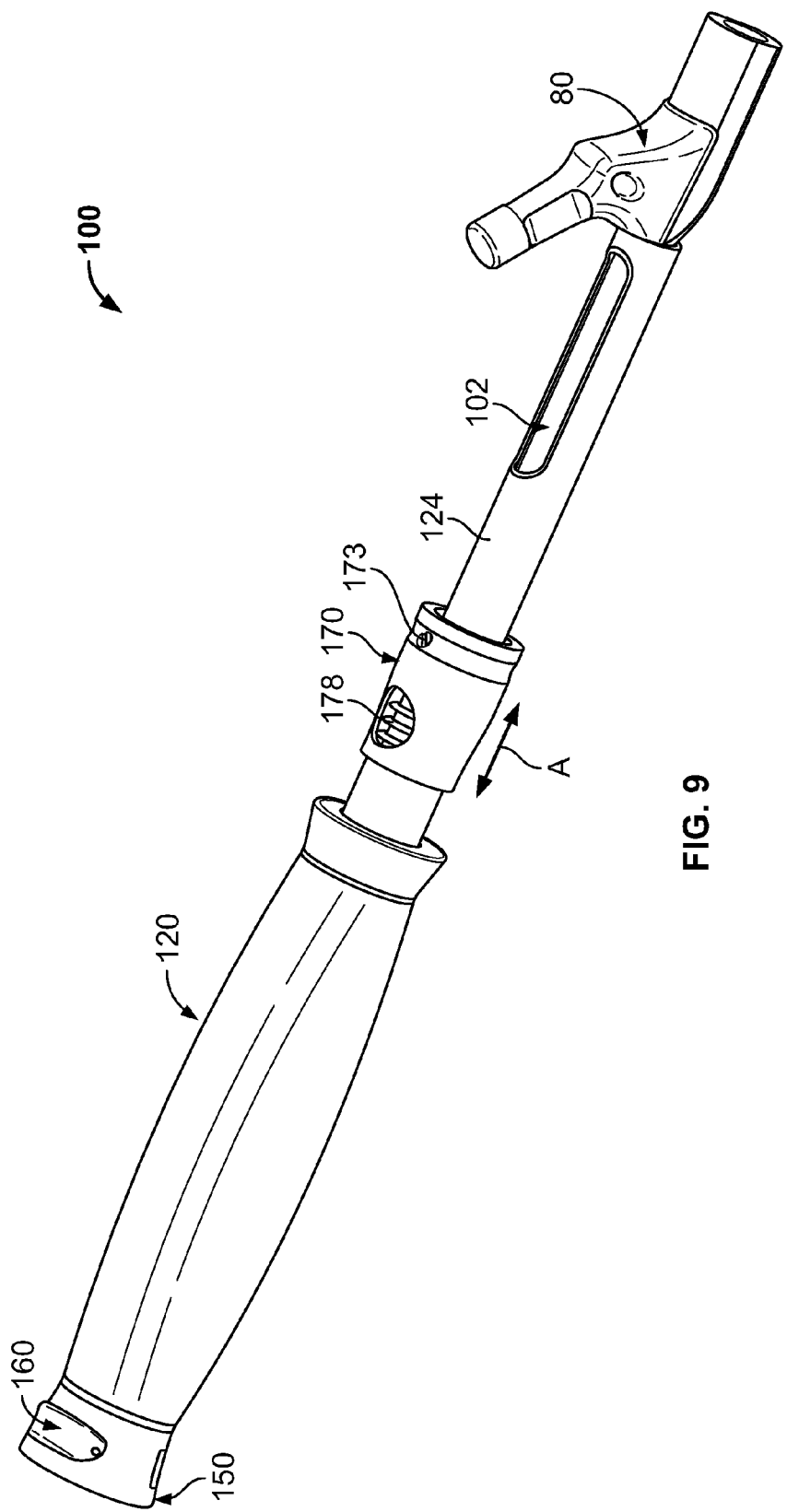
FIG. 9 is an isometric view illustrating the handle member of FIG. 3 assembled over the proximal implant fastener according to the present teachings.
Figure 15:
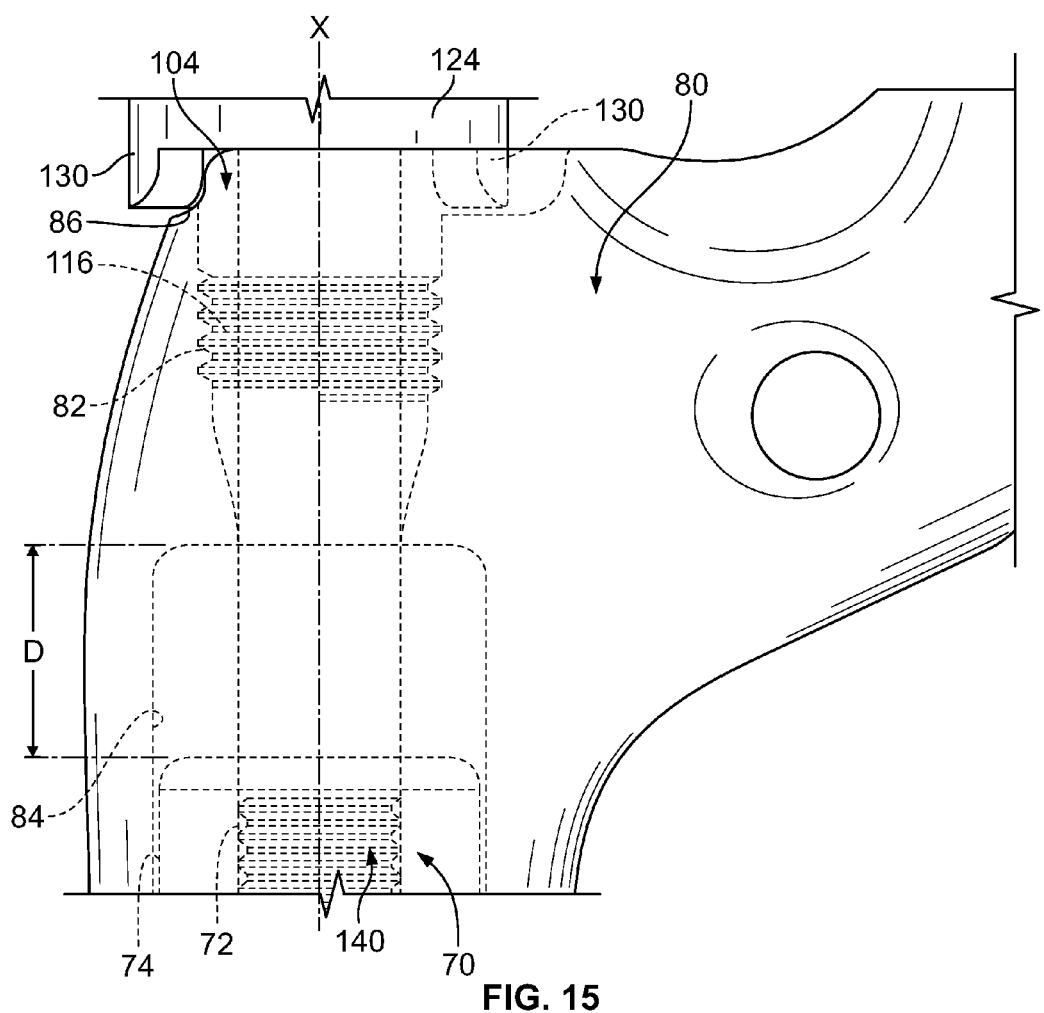
FIG. 15 is a detail of the fully assembled assembly view of FIG. 14, illustrating a separation distance between corresponding tapers of the proximal and distal implants.

Referring to FIG. 2, the first coupler 102 can be a tubular shaft extending between a proximal end 106 and a distal end 104 and having an internal through bore 114. The first coupler 102 can include an external circumferential groove 108 for removable coupling with the handle member 120 and the locking member 170, as discussed below. A distal portion 116 of the first coupler 102 can be configured for coupling to a first or proximal implant 80 of a modular implant assembly, as shown in FIGS. 8 and 15. The distal portion 116 can be, for example, externally threaded and threadably engageable with an internally threaded bore 82 of the proximal implant 80. The first coupler 102 can be engaged to the proximal implant 80 by engaging the distal portion 116 of the first coupler 102 to a bore 82 of the proximal implant 80 (shown in FIG. 15). The first coupler 102 can be rotated either manually or by using a driver to engage a driver-engageable proximal portion 118 of the first coupler 102, as shown in FIG. 8. The first coupler 102 and the proximal implant 80 can be threadably engaged, as illustrated in FIG. 15, although other coupling engagements can also be used. The handle member 120 can be positioned concentrically over the first coupler 102 through the bore 132 of the handle member 120, such that the first coupler 102 is received in the bore 132. The handle member 120 can be locked onto the first coupler 102 by axially moving the quick-connect locking member 170, as shown in FIGS. 9 and 10 and discussed below.

Figure 10:
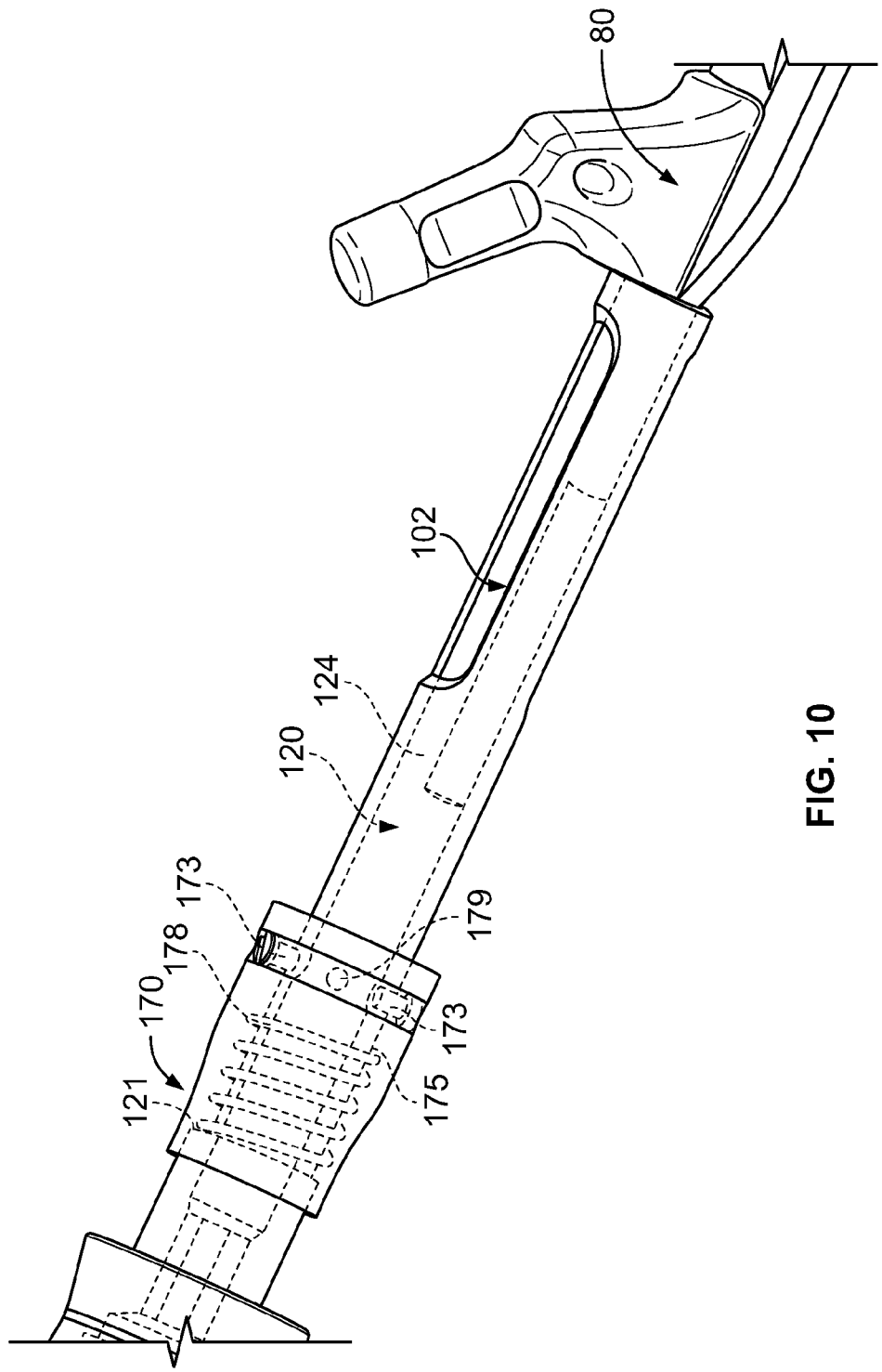
FIG. 10 is an isometric view of a detail of FIG. 9 illustrating a locking member between the handle member and the proximal implant fastener according to the present teachings.

Referring to FIGS. 1, 1A-1C, 6, 9 and 10, the locking member 170 can include a sleeve 171 having a longitudinal bore 172. The sleeve 171 can be spring-loaded onto to the handle member 120 with a spring 178 received within the bore 172 of the sleeve 171 over the tubular shaft 124 of the handle member 120. The spring 178 can be constrained in the sleeve 171 between a circumferential outer shoulder 123 of the handle member 120 and a circumferential inner shoulder 175 of the sleeve 171. The sleeve 171 can be movably supported on the shaft 124 of the handle member 120 along the longitudinal direction of the handle member 120, as indicated with double arrow A in FIG. 1A. In the exemplary embodiment illustrated in FIGS. 1A-1D and 10, a pair of diametrically opposed set screws or pins 173 can pass through holes 174 of the sleeve 171 and through elongated through slots 125. The pins 173 allow the sleeve 171 to move against the bias of the spring 178 relative to the first coupler 102 until a pair of ball bearings 179 engage the groove 108 of the first coupler 102 through holes 129 of the shaft 124 of the handle member 120 to lock the first coupler 102 to the handle member 120. The ball bearings 179 can be positioned within the sleeve 171 circumferentially at 90 degrees relative to the pins 173, as shown in FIGS. 3 and 10. The locking member 170 releasably couples the handle member 120 to the first coupler 102 in a quick-release manner.

Referring to FIGS. 7, 1A-1D and 9, the handle member 120 can be assembled with a slider 160, which defines an eccentric or asymmetric opening 162. The slider 160 is supported within the handle member 120 and is held against the action of two springs 168 by a dowel 169, as shown in FIG. 1D. The dowel 169 is received through a top opening 127 of the distal portion 122 of the handle member 120 and is held against an external slot 166 of the slider 160. The slider 160 can partially obstruct the longitudinal bore 132 of the handle member, as shown in FIG. 1D. A curved portion 161 of the slider 160 extends through an arcuate slot 135. The curved portion 161 can be pushed inward in the direction of arrow B against the action of the springs 168, such that the bore 132 is not obstructed. The function of the slider 160 is further discussed below.

Figure 11:
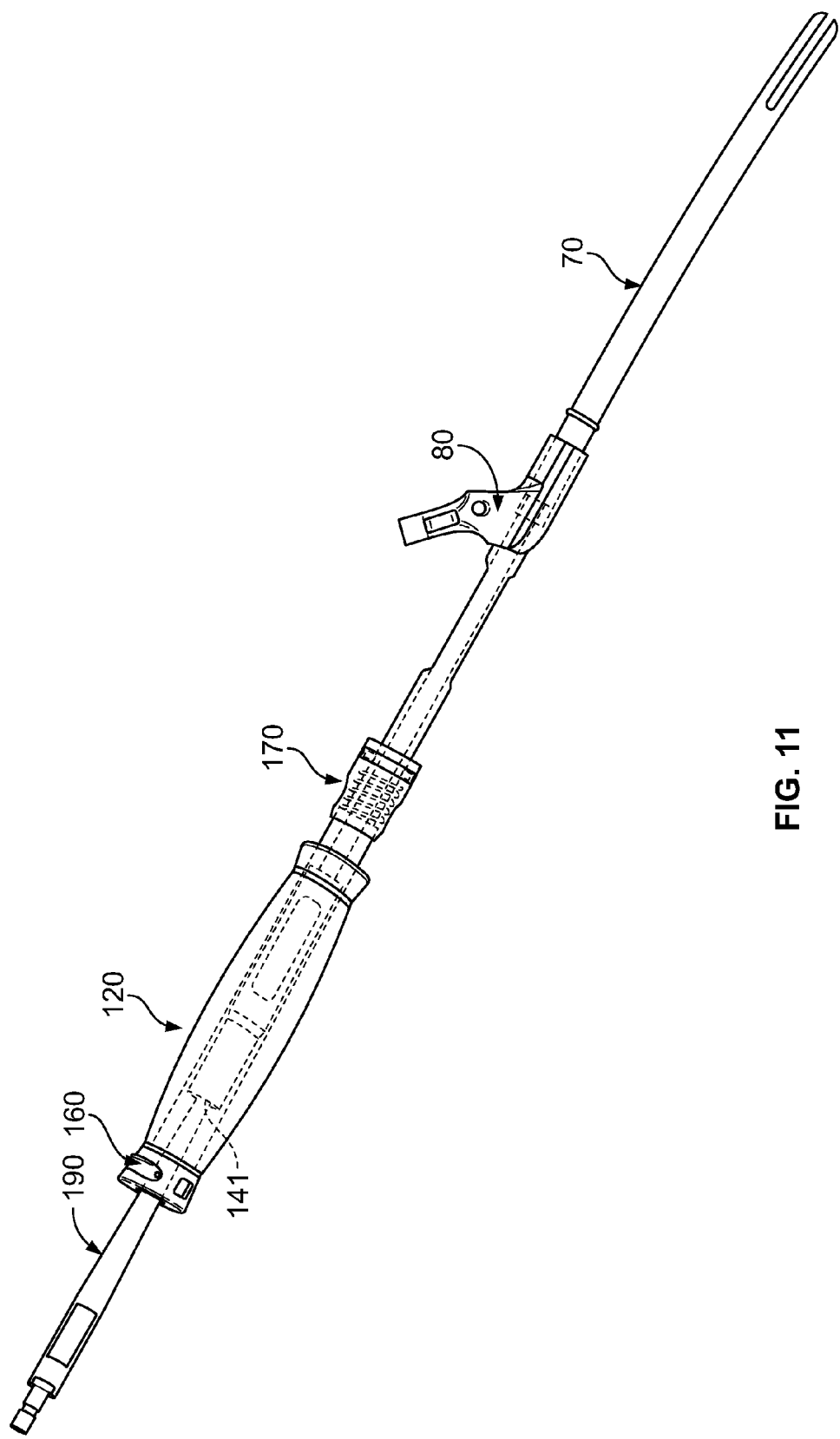
FIG. 11 is an isometric view illustrating the distal implant fastener engaging a distal implant through the assembly of FIG. 9 according to the present teachings.

Referring to FIGS. 4, 1A-1D, and 11-13, the second coupler 140 can include a proximal shaft portion 146, an intermediate shaft portion 144, a distal shaft portion 142 and an externally threaded distal tip portion 148. The various portions 146, 144, 142, 148 can have different diameters, such that corresponding shoulders 143, 145 and 146 are defined therebetween, as shown in FIG. 4. The proximal shaft portion 146 can be externally threaded for engaging the compression member 150, as discussed below. The proximal and distal implants 80, 70 can be aligned and held manually against one another. The second coupler 140 can be concentrically received through the handle member 120, through the bore 114 of the first coupler 102 and through the proximal implant 80 to engage a second or distal implant 70 for coupling the proximal implant 80 and the distal implant 70 of the modular implant assembly, as illustrated in FIG. 11. A driver 190 can be used to engage a driver engagement formation 141 of the proximal shaft portion 146 of the second coupler 140 and rotatably engage the threaded distal tip portion 148 to internal threaded bore 72 of a distal implant 70, as illustrated in FIGS. 11 and 15.

Figure 14:
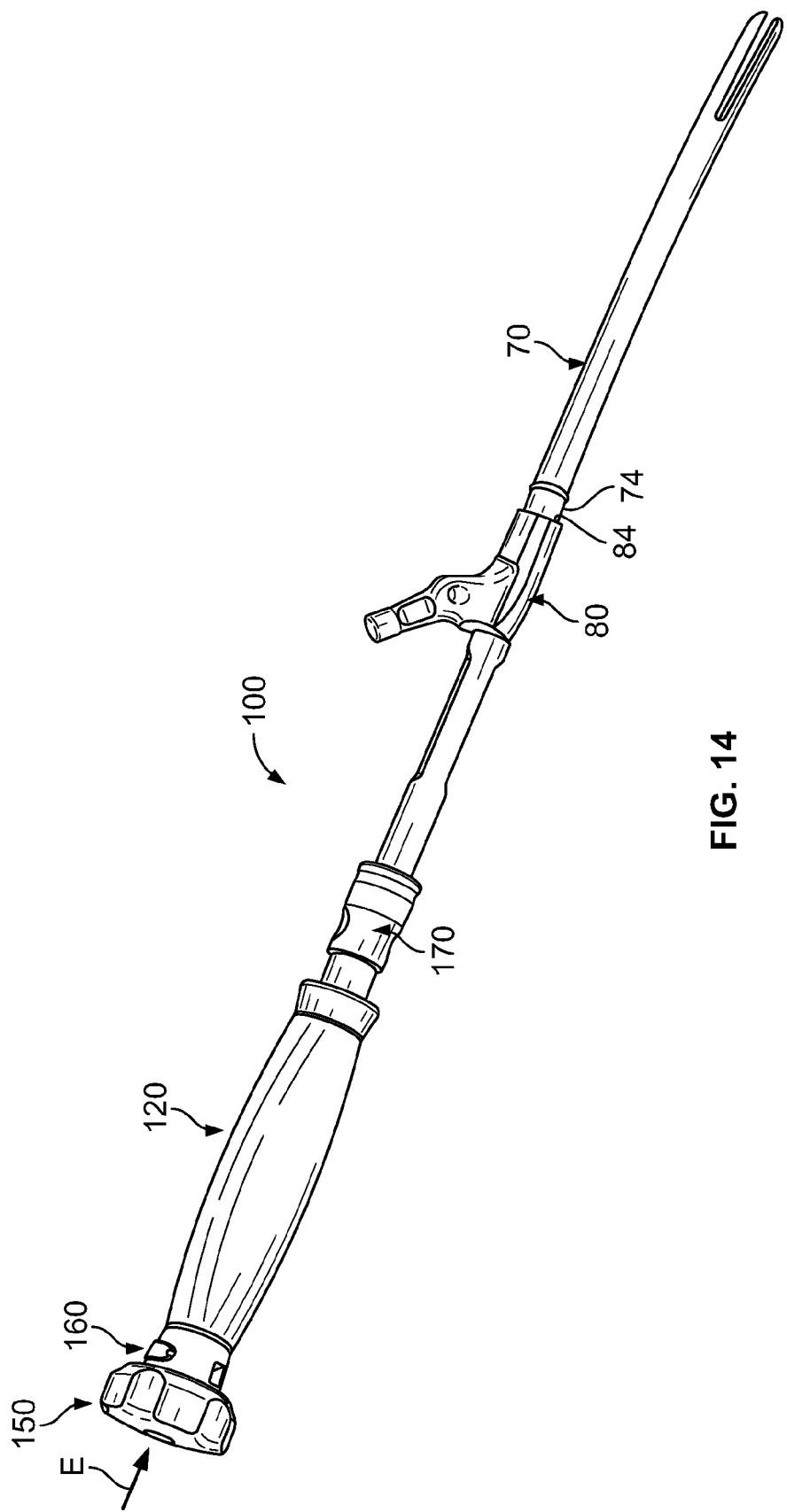
FIG. 14 is an isometric view illustrating the fully assembled assembly tool during impaction according to the present teachings.

As illustrated in FIGS. 12, 14 and 15, the proximal implant 80 can be a proximal femoral body and the distal implant 70 can be a distal femoral stem 70. The proximal and distal implants 80, 70 can include corresponding female and male interlocking tapers 84, 74. As shown in FIG. 15, the interlocking tapers 84, 74 can remain separated and not fully locked during insertion.

Referring to FIGS. 5, 1A-1D and 12-13, the compression member 150 can include a knob portion 152 and a tubular shaft 154. The knob portion 152 can include thumb grooves 159 or other engagement features for rotating the compression member 150. The knob portion 152 can also include an attachment recess 151 for engaging a driver, such as a wrench. The compression member 150 can also include a circumferential groove 158, which can engage the slider 160, as discussed below. The shaft 154 of the compression member 150 can include an internal threaded bore 156, which can be threadably engaged with the externally threaded proximal shaft portion 146 of the second coupler 140. Pushing the slider 160 inward in the direction of arrow B, allows the tubular shaft 154 to be inserted through the longitudinal bore 132 of the handle member 120, as described in connection with FIG. 1D above.

With continued reference to FIGS. 12 and 13, by rotating the knob portion 152 in the direction of curved arrow C, the tubular shaft 154 moves longitudinally and threadably engages the tubular shaft 154 to the proximal shaft portion 146 of the second coupler 140. When the tubular shaft 154 is threaded to the proximal shaft portion 146 along a predetermined length, the slider 160 reaches the level of the circumferential groove 158 and springs into engagement with the circumferential groove 158 with an audible sound or click. The audible sound can signify that the assembly tool 100 is assembled onto the proximal and distal implants 80 and 70, holding the proximal and distal implants at a relative position or distance for implantation. As discussed above, the assembled proximal and distal implants 80, 70 are kept with their respective female and male tapers 84, 74 separated by a distance "D" and are not fully locked, as shown in FIG. 15. The assembly tool 100 can be used to insert the proximal and distal implants 80, 70 into the prepared anatomic site, such as, for example, the patient's femoral bone.

As shown in FIG. 14, the proximal and distal implants 80, 40 can be implanted by axially impacting the upper surface of the compression member 150 in the direction of arrow E. While the assembly tool 100 is impacted in situ and moves such that the distal implant 70 reaches a final seated depth in the anatomic site, version control is available for selection by the medical professional. In particular, the anti-rotational tabs 130 of the handle member 120 can engage corresponding slots 86 defined on the proximal outer surface of the proximal implant 80, such that rotating the handle portion 121 of the handle member 120 about the longitudinal axis X during axial impaction can rotate the handle member 120 and the attached the proximal implant 80 until a selected rotational orientation or version about the axis X is achieved. Impaction does not affect the separation distance D of the female and male tapers 84, 74 of the proximal and distal implants 80, 70 which are held apart by the structural features of the slider 160, the compression member 150 and the first and second couplers 102, 140, as discussed above.

Figure 16:
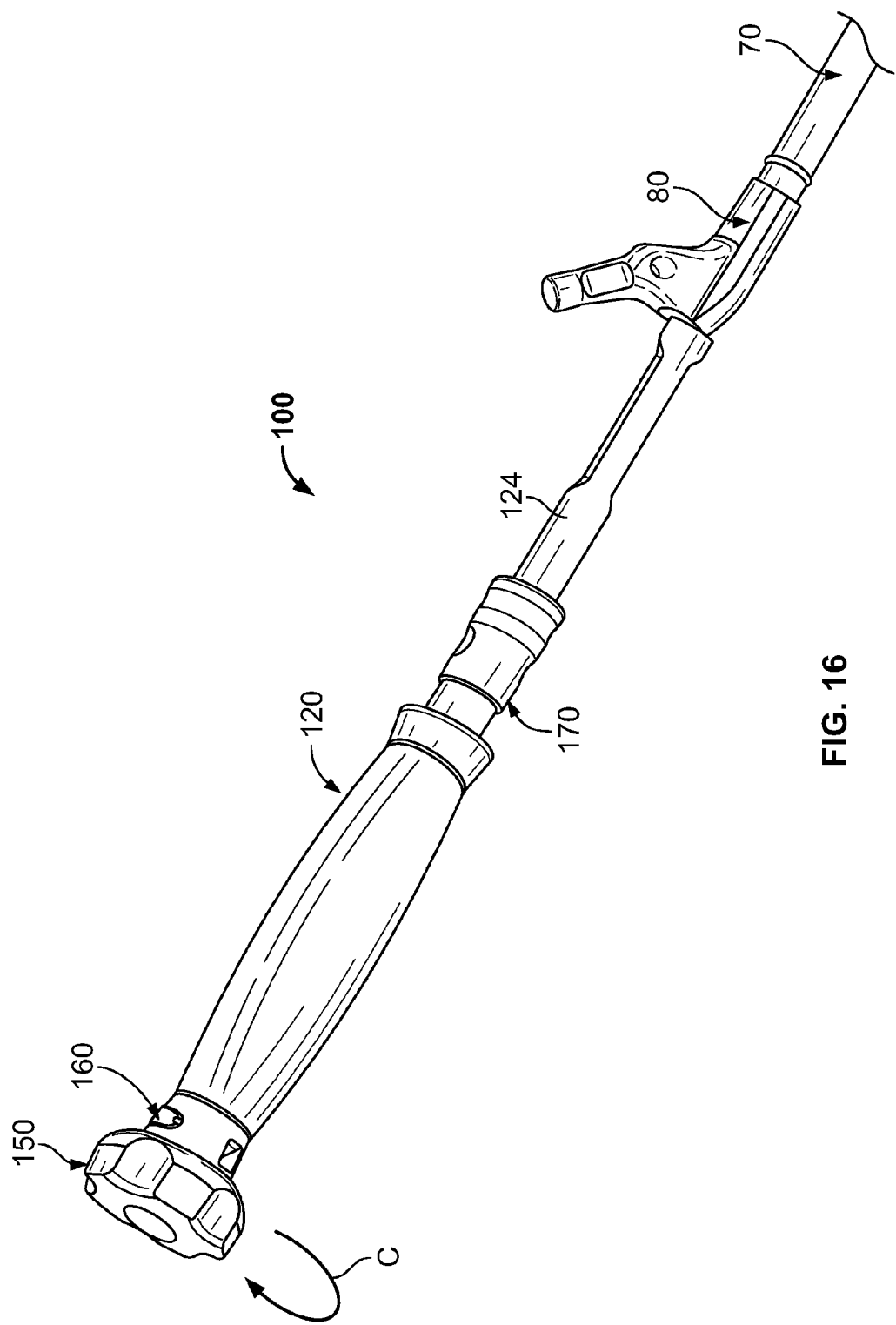
FIG. 16 is an isometric view illustrating the rotation of a compression member of the assembly tool after impaction according to the present teachings.
Figure 17:
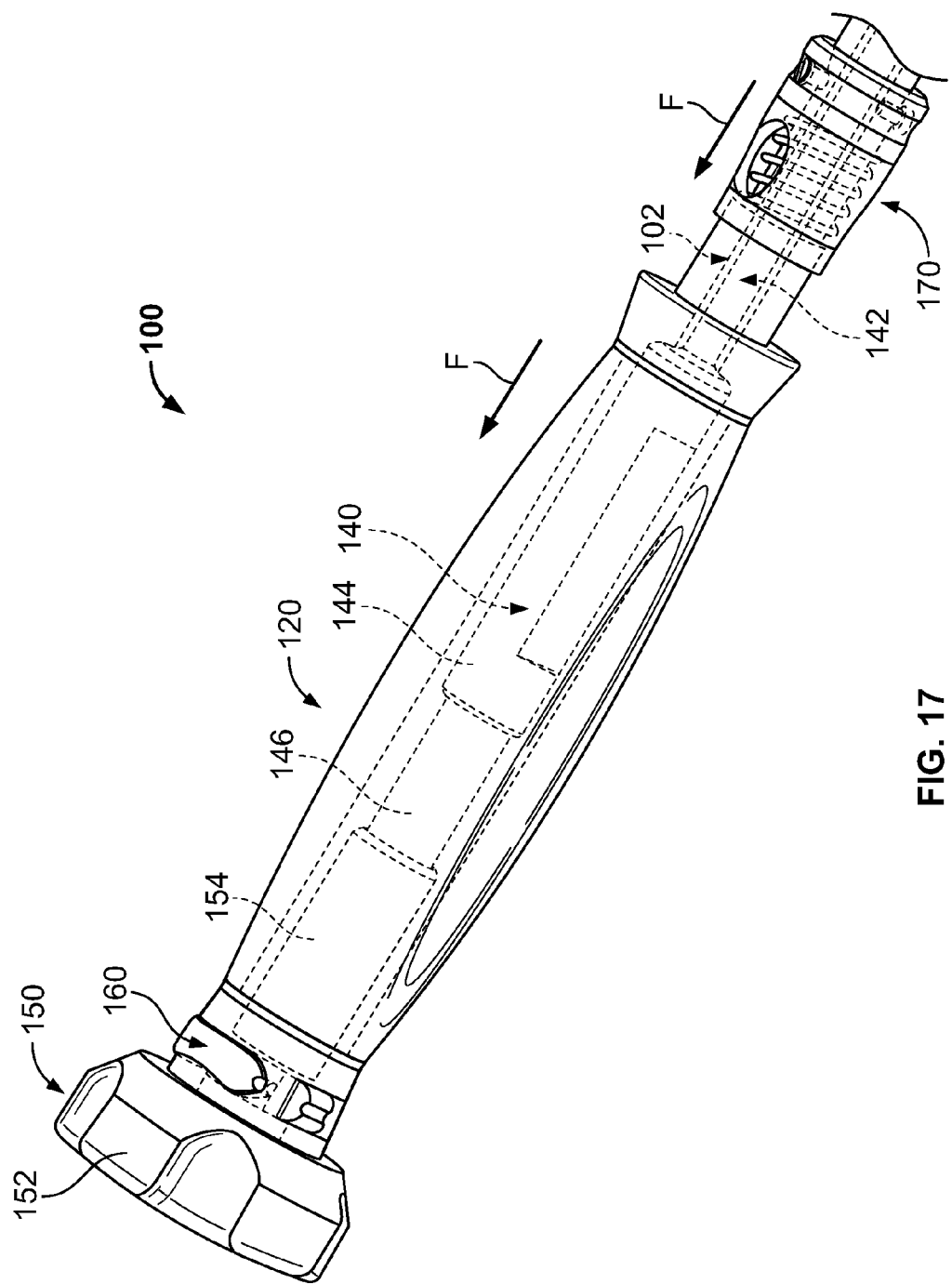
FIG. 17 is a detail of FIG. 16 illustrating a movement of the distal implant fastener reducing the separation distance of FIG. 15 during rotation of the compression member illustrated in FIG. 16 according to the present teachings.

Referring to FIGS. 16 and 17, rotating further the compression member 150 in the direction of arrow C to further tighten the compression member 150 draws the second coupler 140 proximally in the direction of arrow F and reduces or closes the separation distance of the respective female and male tapers 84, 74, thereby securely locking the proximal and distal implants 80, 70 to one another in situ and without removing the assembly tool 100. Rotation of the compression member 150 for fully locking the corresponding tapers 84, 74 of the proximal and distal implants 80, 70 to one another can be facilitated by engaging a wrench or other driver to the attachment feature 151 (shown in FIG. 1C) of the compression member.

Summarizing, the assembly tool 100 can be assembled onto the proximal and distal implants 80, 70 sequentially, by first coupling the first coupler 102 to the proximal implant 80 and then assembling the handle member 120 over the first coupler 102 by a quick connection using the locking member 170. The second coupler 140 can be inserted coaxially through the first coupler 102 and through the proximal implant 80 to engage the distal implant 70. Finally, the compression member 150 can be coupled to the handle member 120 and can be engaged to the distal shaft portion 142 of the second coupler 140.

After the proximal and distal implants 80, 70 are fully locked to one another, the assembly tool 100 can be disassembled and removed in the reverse procedure while the tapers 84, 74 of the proximal and distal implants 80, 70 remain securely locked. Specifically, the compression member 150 can be first unscrewed and removed. The second coupler 140 is then unscrewed and removed, followed by the handle member 120 which is released from the first coupler 102 using the locking member 170. The first coupler 102 is then unscrewed and removed.

As discussed above, the assembly tool 100 can be modularly and sequentially assembled onto the proximal and distal implants 80, 70, while holding the respective connecting tapers of the proximal and distal implants 80, 70 at a selected separation distance D. The proximal and distal implants can be impacted into the anatomic site at their final seating depth by impacting the compression member of the assembly tool 100, which is still assembled thereon. Before or during impaction, the implant version can be selected while the assembly tool 100 is fully engaged, by rotating the handle member 120 of the assembly tool 100, without affecting the separation distance D. After the version is selected and the implants are fully seated, the compression member 150 of the assembly tool 100 can be rotated in situ to reduce the separation distance D and lock corresponding tapers 84, 74 of the proximal and distal implants 80, 70. After the tapers 84, 74 of the proximal and distal implants 80, 70 are fully locked and secured, the components of the assembly tool 100 can be disassembled in reverse order of assembly and the assembly tool 100 removed.

It will be appreciated from the above discussion, that the assembly tool 100 can facilitate the procedure of implanting and securing modular components in a sequential manner that guides and assist the medical professional by providing an efficacious in situ assembly and disassembly.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for implanting a modular implant having a proximal implant and a distal implant into an anatomic site, the method comprising:
    engaging a distal portion of a first coupler to the proximal implant;
    releasably connecting a handle member to the first coupler;
    passing a second coupler through the handle member and the first coupler;
    engaging a distal portion of the second coupler through the proximal implant to the distal implant;
    engaging a compression member to a proximal portion of the second coupler extending through the handle member;
    rotating the compression member to hold corresponding tapers of the proximal and distal implants separated by a selected separation distance;
    impacting the proximal and distal implants to an anatomic depth by impacting the compression member while holding the tapers separated by the separation distance; and
    rotating the compression member to reduce the separation distance and fully lock the corresponding tapers of the proximal and distal implants without removing the compression member.

2. The method of claim 1, wherein releasably connecting the handle member to the first coupler includes actuating a locking member coupled to the handle member.

3. The method of claim 1, further comprising:
    engaging an anti-rotation tab of the handle member to a groove of the proximal implant; and
    rotating the handle member while impacting the compression member to a selected version of the proximal implant.

4. The method of claim 1, wherein engaging the distal portion of the second coupler to the distal implant comprises threadably engaging the distal portion of the second coupler to an inner bore of the distal implant.

5. The method of claim 4, wherein engaging the compression member to the proximal portion of the second coupler comprises threadably engaging the compression member to the proximal portion.

6. The method of claim 1, further comprising removing the compression member from the second coupler without unlocking the corresponding tapers of the proximal and distal implants.

7. The method of claim 6, wherein removing the compression member comprises threadably disengaging the compression member from the proximal portion of the second coupler.

8. The method of claim 6, further comprising threadably disengaging the distal portion of the second coupler from the distal implant and removing the second coupler.

9. The method of claim 8, further comprising releasing the handle member from the first coupler by operating a spring-actuated locking member.

10. The method of claim 9, further comprising disengaging and removing the first coupler from the proximal implant.

11. A method for implanting a modular implant having a proximal implant and a distal implant into an anatomic site, the method comprising:
    sequentially assembling a modular assembly tool on to the proximal and distal implants;
    holding corresponding tapers of the proximal and distal implants separated by a selected separation distance by the assembly tool;
    impacting the proximal and distal implants to an anatomic depth without changing the separation distance by impacting the assembly tool; and
    actuating the assembly tool to fully lock the corresponding tapers of the proximal and distal implants and reduce the separation distance without removing the assembly tool.

12. The method of claim 11, wherein actuating the assembly tool comprises rotating a compression member of the assembly tool.

13. The method of claim 11, further comprising selecting a version of the proximal implant while impacting the assembly tool.

14. The method of claim 11, further comprising disassembling the modular assembly tool in reverse of the order of assembly.

15. The method of claim 11, wherein sequentially assembling a plurality of components of an assembly tool on to the proximal and distal implants includes:
    engaging a distal portion of a first coupler to the proximal implant;
    releasably connecting a handle member to the first coupler;
    passing a second coupler through the handle member and the first coupler;
    engaging a distal portion of the second coupler through the proximal implant to the distal implant; and
    engaging a compression member to a proximal portion of the second coupler through the handle member.

16. The method of claim 15, further comprising disassembling the assembly tool without unlocking the tapers of the first and second implants by sequentially disengaging and removing the compression member, the second coupler, the handle member and the first coupler.

17. A method for implanting a modular implant having a proximal implant and a distal implant into an anatomic site, the method comprising:
    assembling an assembly tool having a handle member, a proximal implant fastener, a distal implant fastener, and a compression member on to the proximal and distal implants along a longitudinal axis, such that the handle member is coupled to the proximal implant fastener and the distal implant fastener extends through the handle member and the proximal implant fastener and is coupled to the compression member;

rotating the compression member relative to the handle member by a first amount to hold corresponding tapers of the proximal and distal implants separated by a selected separation distance;

impacting the proximal and distal implants to an anatomic depth without changing the separation distance by impacting the assembly tool; and rotating the compression member by a second amount to fully lock the corresponding tapers of the proximal and distal implants and reduce the separation distance without removing the assembly tool.

18. The method of claim 17, wherein impacting the assembly tool comprises impacting an impaction surface of the compression member.

19. The method of claim 18, further comprising rotating the handle member to a selected version of the proximal implant while impacting the compression member.

20. The method of claim 17, further comprising sequentially disassembling the assembly tool in reverse of the order of assembly.

* * * * *